(12) United States Patent
Yamauchi et al.

(10) Patent No.: US 6,679,919 B2
(45) Date of Patent: *Jan. 20, 2004

(54) ARTIFICIAL DURA

(75) Inventors: Koji Yamauchi, Ayabe (JP); Tomohiko Asahara, Koto-ku (JP)

(73) Assignee: Gunze Limited, Kyoto (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/529,758

(22) PCT Filed: Oct. 7, 1998

(86) PCT No.: PCT/JP98/04542

§ 371 (c)(1),
(2), (4) Date: Apr. 19, 2000

(87) PCT Pub. No.: WO99/20320

PCT Pub. Date: Apr. 29, 1999

(65) Prior Publication Data

US 2003/0014125 A1 Jan. 16, 2003

(30) Foreign Application Priority Data

Oct. 22, 1997 (JP) ............................................... 9-290016

(51) Int. Cl.7 .................................................. A61F 2/36
(52) U.S. Cl. .................................. 623/23.72; 623/23.75
(58) Field of Search ................. 623/11, 23.72, 623/23.75

(56) References Cited

U.S. PATENT DOCUMENTS 5,861,034 A * 1/1999 Taira et al. ................... 623/11

FOREIGN PATENT DOCUMENTS

| EP | 0325195 | 7/1989 | |
| EP | 0423155 | 4/1991 | |
| JP | 2152461 | 6/1990 | |
| JP | 3505535 | 12/1991 | |
| JP | 8080344 | * 9/1994 | ............ A61F/2/02 |
| JP | 880344 | 3/1996 | |

OTHER PUBLICATIONS

Noshinkeigeka, vol. 21 No. 2, pp 167–70 (1993).
Journal of Biomedical Materials Research, vol. 25 pp 267–76 (1991).
No to Shinkei, vol. 21 pp 1089–98 (1969).
JP8080344A2—Abstract.
"Development of Dural Substitute From Synthetic Bioabsorbable Polymers" by Yamada et al., *J. Neurosurg.*, vol. 86, Jun. 1997, pp. 1012–1017.
European Search Report dated Aug. 6, 2002.

* cited by examiner

*Primary Examiner*—Corrine McDermott
*Assistant Examiner*—Thomas C. Barrett
(74) *Attorney, Agent, or Firm*—Baker Botts L.L.P.

(57) ABSTRACT

The present invention provides an artificial dura mater prepared from an biodegradable and bioabsorbable synthetic polymer sheet and having a total light transmittance of 30% or more as defined by JIS K7105, a haze (cloudiness value) of 80% or less as defined by JIS K7105 or a specular glossiness at 60° (Gs 60°) of 10–20% as defined by JIS Z8741.

19 Claims, 3 Drawing Sheets

ARTIFICIAL DURA

CROSS-REFERENCE TO RELATED APPLICATIONS

This application is a national phase application of International Application No. PCT/JP98/04542, which was filed Oct. 7, 1998 and which published in Japanese on Apr. 29, 1999 which in turn claims priority from Japanese Application No. 9/290 016, which was filed on Oct. 22, 1997.

TECHNICAL FIELD

The present invention relates to an artificial dura mater to be used for prosthesis of dural defect in the field of neurosurgery and a method for treating the dural defect.

BACKGROUND ART

The dura mater occurring between the cranial bones and brain and covering the spinal cord protects the brain and spinal cord and inhibits leakage of cerebrospinal fluid. In the field of neurosurgery, a defect or contracture of the dura mater used to be filled with lyophilized products of human dura mater. However, the lyophilized products of human dura mater had drawbacks such as low homogeneity and short supply. Further, a possible transmission of infection of Creutzfelt-Jacob disease through the use of the human dura mater was reported (Noshinkeigeka; 21(2), 167–170, 1993) and, eventually, the Japanese Ministry of Health and Welfare banned the use of the lyophilized product of human dura mater on Apr. 7, 1997.

To solve the above drawbacks, artificial dura mater made of silicone, for example, was developed. However, the silicone dura mater has fallen into disuse as it was reported that the silicone dura mater predisposed to meningorrhagia by remaining in vivo permanently because it was non-biodegradable, whereby being a chronic stimulant for the surrounding tissue to cause hypertrophy of the granulation tissue.

In contrast, artificial dura maters made of biodegradable and bioabsorbable materials such as collagen (Journal of Biomedical Materials Research; Vol. 25 267–276, 1991) and gelatin (No to Shinkei; 21 1089–1098, 1969) were produced, but they were not in practical use because of strength-related problems, i.e., because of the insufficiency in the suture strength to be sutured integrally with the internal dura mater.

The applicant provided, in Japanese Unexamined Patent Publication No. 8-80344, an artificial dura mater comprising a sheet made of a biodegradable and bioabsorbable polymer, for example, a copolymer of lactic acid and caprolactone and, further, an artificial dura mater comprising introducing a biodegradable and bioabsorbable polymer made of a material different from that of the sheet as a reinforcement between the sheets and integrally molding the sheets and the reinforcement.

An object of the present invention is to provide an artificial dura mater which allows to observe the brain surface therethrough after covering the operative field with the artificial dura mater.

Another object of the present invention is to provide a method for treating dural defect.

DISCLOSURE OF INVENTION

Figure 1:
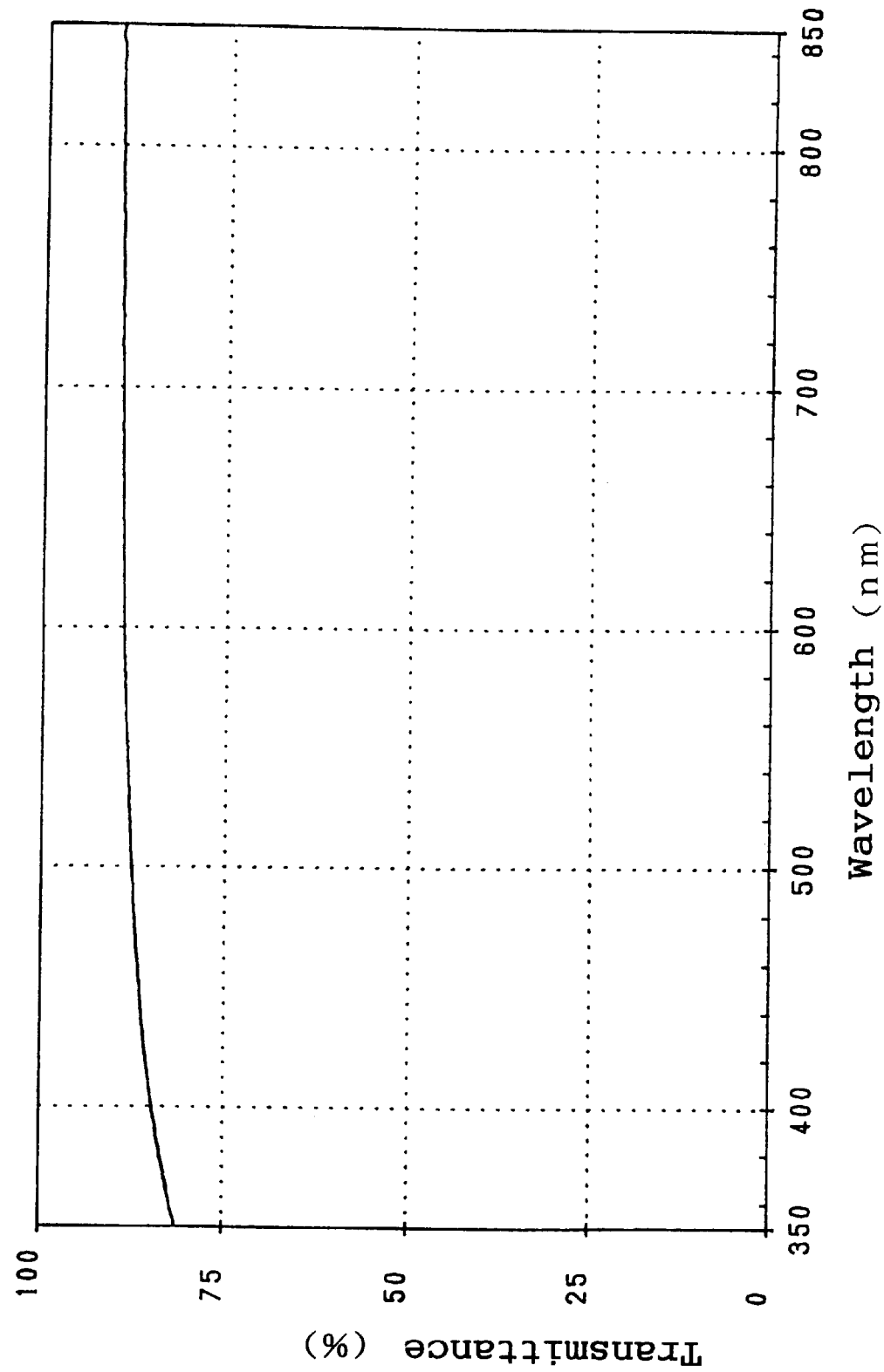
FIG. 1 is a spectrum showing a total light transmittance of the artificial dura mater obtained in Example 1 of the present invention.

An artificial dura mater of the present invention is characterized by comprising a biodegradable and bioabsorbable synthetic polymer sheet, and having a total light transmittance of 30% or more as defined by Japanese Industrial Standard JIS K7105.

Further, an artificial dura mater of the present invention is characterized by comprising a biodegradable and bioabsorbable synthetic polymer sheet, and having a haze (cloudiness value) of 80% or less as defined by JIS K7105.

Moreover, artificial dura mater of the present invention is characterized by comprising a biodegradable and bioabsorbable synthetic polymer sheet, and having a specular glossiness at 60° (Gs 60°) of 10–20% as defined by JIS Z8741.

The present invention further provides a method for treating a dural defect which comprises covering the dural defect by suturing the residual native dura mater intergrally with an artificial dura mater according to the invention.

According to the invention, Examples of the biodegradable and bioabsorbable synthetic polymer are aliphatic polyesters (polyglycolic acid, polylactic acid, polycaprolactone, polyvalerolactone and copolymers thereof), polyesterether (poly-1,4-dioxanone-2-one, poly-1,5-dioxepan-2-one, ethyleneglycol-said aliphatic polyester copolymer, propyleneglycol-said aliphatic polyester copolymer) and copolymers of the aliphatic polyester and polyesterether, preferably a copolymer of lactic acid (L form, D form, D,L form) and caprolactone, more preferably a copolymer of L-lactic acid and ε-caprolactone.

The artificial dura mater of the invention has a total light transmittance of about 30% or more, preferably about 50% or more, more preferably about 70% or more as defined by JIS K7105.

A haze (cloudiness value) of the artificial dura mater may preferably be about 80% or less, more preferably about 70% or less.

A specular glossiness at 60° (Gs 60°) of the artificial dura mater may preferably be about 10–20%, more preferably be about 15–18%.

Examples of a preferable artificial dura mater of the invention are an artificial dura mater having a total light transmittance of about 30% or more as defined by JIS K7105 and a haze (cloudiness value) of about 80% or less as defined by JIS K7105, especially an artificial dura mater having a total light transmittance of about 70% or more and a haze (cloudiness value) of about 70% or less.

The artificial dura mater of the invention may especially preferably have a total light transmittance of about 70% or more, haze (cloudiness value) of about 70% or less and a GS 60° of about 15–18%.

If at least one of the total light transmittance, haze (cloudiness value) and GS 60° is in the above range, the sheet to be used is not limited to said biodegradable and bioabsorbable synthetic polymer sheet.

In addition, the artificial dura mater of the invention may be foamed or in the form of a porous film having micropores.

If the total light transmittance is lower than 30% as defined by JIS K7105, it will be difficult to observe the brain surface through the resultant artificial dura mater. Also, if the haze (cloudiness value) is higher than 80% as defined by JIS K7105, it will be difficult to observe the brain surface through the resultant artificial dura mater.

BEST MODE FOR CARRYING OUT THE INVENTION

The following example serves to illustrate the present invention. It is to be understood that the example is not restrictive of the present invention.

EXAMPLE 1

1. Production of Polymer
(1) Film (Sheet) Portion

L-lactide/ε-caprolactone copolymer [molar ratio: 50/50; weight average molecular weight by GPC: 150,000; hereinafter referred to as P (L-LA/CL) (molar ratio: 50/50)] was synthesized in a conventional manner.

(2) Reinforcement (Nonwoven Fabric) Portion

Polyglycolic acid (intrinsic viscosity=1.18) was produced in a conventional manner.

2. Production of Film (Sheet)

1. P (L-LA/CL) (molar ratio: 50/50) obtained in (1) was dissolved in a solvent (chloroform) so that the resultant solution contains 5 wt % of P (L-LA/CL) (molar ratio: 50/50). After completion of dissolution, the solution was subjected to filtration to remove insoluble matter. The solution was then casted on a glass plate (flow casting) and subjected to an air drying, followed by a vacuum drying at 50° C. for 12 hours to remove the solvent completely.

3. Production of Reinforcement (Nonwoven Fabric)

1. A nonwoven fabric was produced by spinning the polyglycolic acid obtained in (2) to obtain a polyglycolic acid yarn having 20 deniers, followed by drawing, and then circular knitting the drawn yarn and needle punching this knitting.

4. Composite

An artificial dura mater having a three-layer structure (film thickness of 200 pm) was produced by integrally molding the reinforcement (nonwoven fabric) obtained in (3) with the films (sheets) obtained in (2) placed at both sides of the reinforcement by vacuum press at a temperature of 140° C. and a pressure of 50 kg/cm$^2$.

(Total Light Transmittance Test)

The artificial dura mater obtained in Example 1, e-PTFE (GORE-TEX (registered trademark)) and a lyophilized cadaveric dura mater (Tutoplast Dura (registered trademark)) respectively were cut into test pieces each having a size of 50 mm×50 mm, and then the transmittance of each of the test pieces was measured by means of an automatic spectrophotometer (UV310PC, manufactured by Shimazu Seisakusho). The measurement results are shown in Table 1 and FIGS. 1–3.

TABLE 1

| | Test Piece | | |
|---|---|---|---|
| Wavelength (nm) | Example 1 | e-PTFE | Cadaveric Dura Mater |
| 350 | 71.7 | 2.4 | 0.1 |
| 550 | 74.2 | 3.9 | 2.3 |
| 850 | 90.0 | 6.3 | 7.0 |

Figure 2:
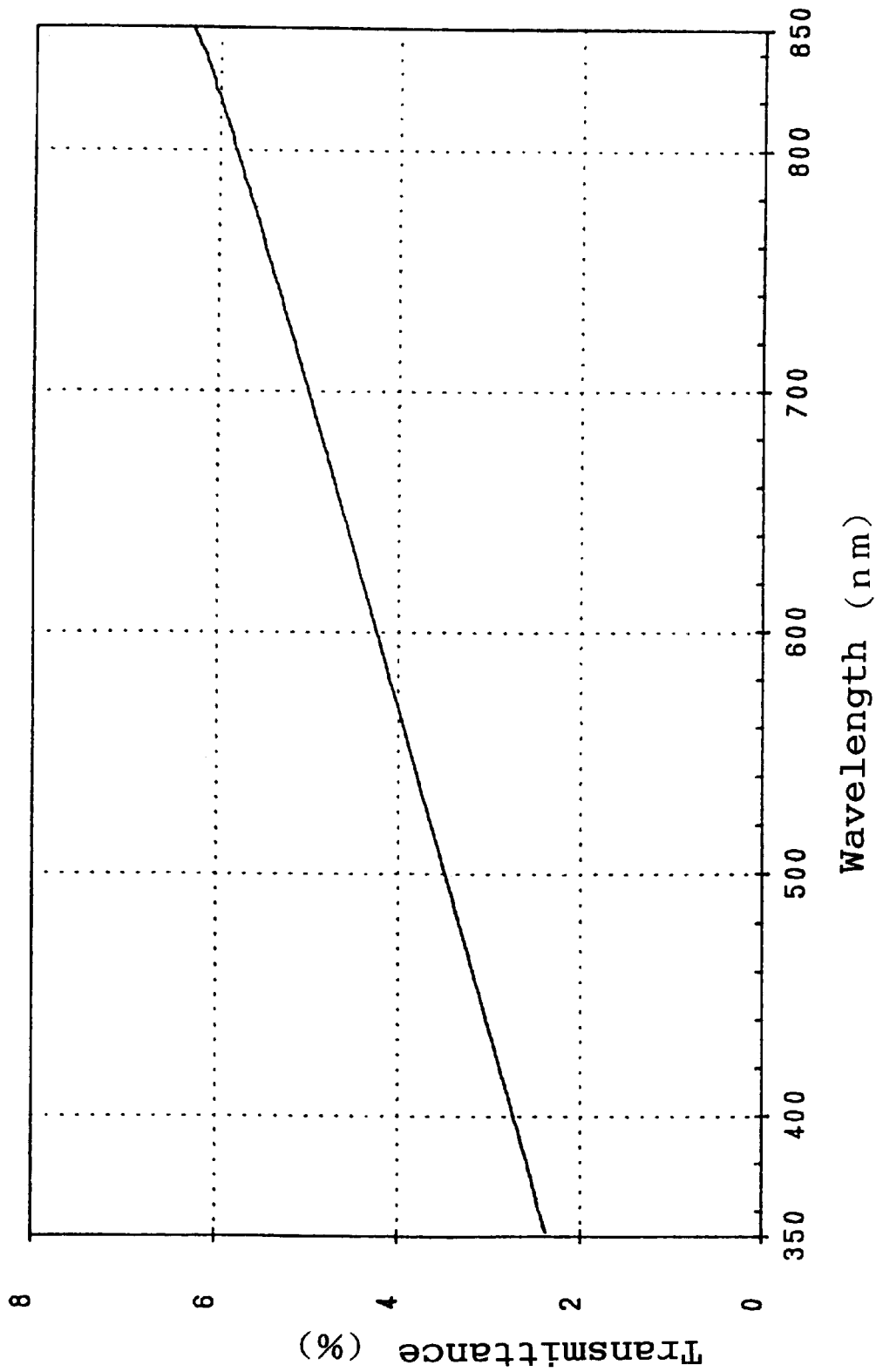
FIG. 2 is a spectrum showing a total light transmittance of e-PTFE manufactured by W. L. Gore & Associates, Inc. (GORE-TEX (registered trademark)).
Figure 3:
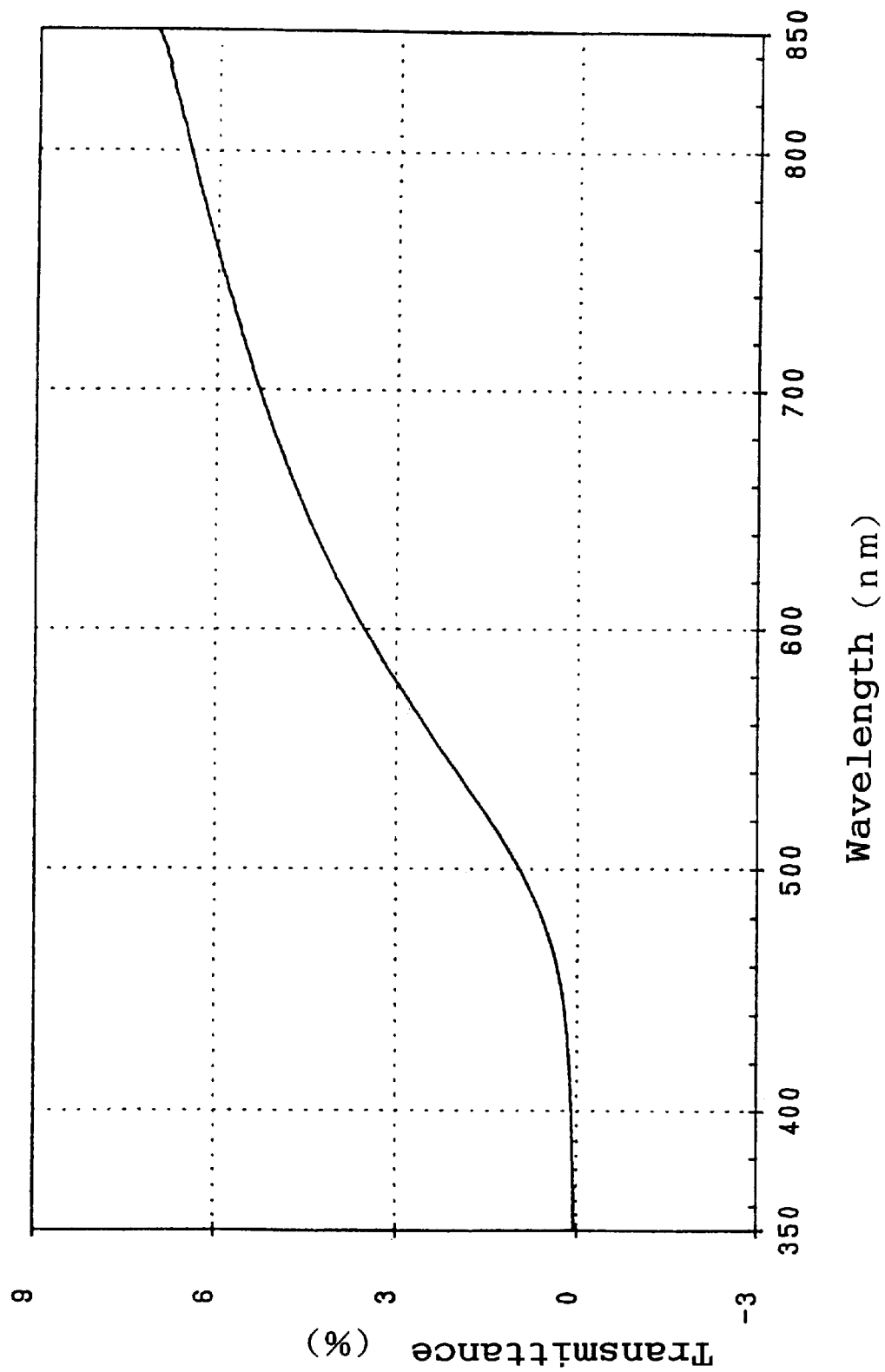
FIG. 3 is a spectrum showing a total light transmittance of a lyophilized cadaveric dura mater manufactured by Tokibo (Tutoplast Dura (registered trademark)).

FIG. 1 shows a transmittance spectrum of the artificial dura mater of the invention obtained in Example 1. FIG. 2 shows a transmittance spectrum of the e-PTFE (GORE-TEX (registered trademark)). FIG. 3 shows a transmittance spectrum of the lyophilized cadaveric dura mater (Tutoplast Dura (registered trademark)).

As is apparent from Table 1 and FIGS. 1–3, the artificial dura mater of the invention have a good transmittance which allows to observe the brain surface therethrough.

(Haze (Cloudiness Value) Test)

The artificial dura mater obtained in Example 1, e-PTFE (GORE-TEX (registered trademark)) and a lyophilized cadaveric dura mater (Tutoplast Dura (registered trademark)) respectively were cut into test pieces each having a size of 50 mm×50 mm, and then the hazes (cloudiness values) of each of the test pieces were tested in accordance with JIS K7105 using a direct-reading haze computer (HGM-2K manufactured by Suga Test Instruments Co., Ltd.). The measurement results are shown in Table 2.

TABLE 2

| | Example 1 | e-PTFE | Cadaveric Dura mater |
|---|---|---|---|
| Haze (Cloudiness Value) | 63.3 | 98.4 | 99.2 |

(Specular Glossiness at 60° (Gs 60°) Test)

The artificial dura mater of the invention obtained in Example 1 was cut into a test piece having a size of 50 mm×50 mm, and then the Gs (60°) of the test piece was measured in accordance with JIS Z8741 by using YGV-5K, a digital deformation glossmeter manufactured by Suga Test Instruments Co., Ltd. The Gs (60°) of the artificial dura mater of Example 1 was measured to be 17.

As explained above, according to the present invention, it is possible to observe the brain surface after covering the operative field with the artificial dura mater of the invention, and the artificial dura mater of the invention is sutured integrally with the internal dura mater easily since the internal dura mater can be observed through the artificial dura mater even during the operation.

We claim:

1. A method for producing an artificial dura mater having a three layer structure comprising biodegradable and bioabsorbable synthetic polymer sheets and a reinforcement prepared from a biodegradable and bioabsorbable synthetic polymer differing from that of sheets, having a specular glossiness at 60° that is greater than 10% but not more than 20% as defined by JIS Z8741, comprising:

(a) sandwiching a reinforcement between the sheets; and
(b) integrally molding the sheets and the inforcement by vacuum press.

2. The method of claim 1, wherein the biodegradable and bioabsorbable synthetic polymer is a polymer selected from the group consisting of aliphatic polyesters (polyglycolic acid, poly(L form, D form, D,L form) lactic acid, polycaprolactone, polyvalerolactone and copolymers thereof), polyesterether (poly-1,4-dioxanone-2-one, poly-1, 5-dioxepan-2-one, ethyleneglycol-said aliphatic polyester copolymer, propyleneglycol-said aliphatic polyester copolymer) and copolymers of the aliphatic polyester and polyesterether.

3. The method of claim 1, wherein the biodegradable and bioabsorbable synthetic polymer is a copolymer of lactic acid and caprolactone.

4. The method of claim 1, wherein the reinforcement is a polymer selected from the group consisting of a lactide/ε- caprolactone copolymer which is different from that of the sheet in the molar ratio, polyglycolic acid, polylactic acid and lactic acid/glycolic acid copolymer.

5. The method of claim 1, wherein the specular glossiness at 60° (GS 60°) of the artificial dura mater is 15–18% as defined by JIS Z8741.

6. A method for producing an artificial dura mater having a three layer structure comprising biodegradable and bioabsorbable synthetic polymer sheets and a reinforcement prepared from a biodegradable and bioabsorbable synthetic polymer differing from that of sheets, having a haze of 80% or less as defined by JIS K7105, comprising:

(a) sandwiching a reinforcement between the sheets; and (b) integrally molding the sheets and by vacuum press.

7. The method of claim 6, wherein the biodegradable and bioabsorbable synthetic polymer is a polymer selected from the group consisting of aliphatic polyesters (polyglycolic acid, poly(L form, D form, D,L form) lactic acid, polycaprolactone, polyvalerolactone and copolymers thereof), polyesterether (poly-1,4-dioxanone-2-one, poly-1,5-dioxepan-2-one, ethyleneglycol-said aliphatic polyester-copolymer, propyleneglycol-said aliphatic polyester copolymer) and copolymers of the aliphatic polyester and polyesterether.

8. The method of claim 6, wherein the biodegradable and bioabsorbable synthetic polymer is a copolymer of lactic acid and caprolaotone.

9. The method of claim 6, wherein the reinforcement is a polymer selected from the group consisting of a lactide/ε-caprolactone copolymer which is different from that of the sheet in the molar ratio, polyglycolic acid, polylactic acid and lactic acid/glycolic acid copolymer.

10. The method of claim 6, specular glossiness at 60° (GS 60°) of the artificial dura mater is 15–18% as defined by JIS Z8741.

11. A method for producing an artificial dura mater having a three layer structure comprising biodegradable and bioabsorbable synthetic polymer sheets and a reinforcement prepared from a biodegradable and bioabsorbable synthetic polymer differing from that of sheets, having a total light transmittance of 30% or more as defined by JIS K7105, comprising:

(a) sandwiching a reinforcement between the sheets; and (b) integrally molding the sheets and the reinforcement by vacuum press.

12. The method of claim 11, wherein the biodegradable and bioabsorbable synthetic polymer is a polymer selected from the group consisting of aliphatic polyesters (polyglycolic acid, poly(L form, D form, D,L form) lactic acid, polycaprolactone, polyvalerolactone and copolymers thereof), polyesterether (poly-1,4-dioxanone-2-one, poly-1,5-dioxepan-2-one, ethyleneglycol-said aliphatic polyester-copolymer, propyleneglycol-said aliphatic polyester copolymer) and copolymers of the aliphatic polyester and polyesterether.

13. The method of claim 11, wherein the biodegradable and bioabsorbable synthetic polymer is a copolymer of lactic acid and caprolaotone.

14. The method of claim 11, wherein the-reinforcement is a polymer selected from the group consisting of a lactide/ε-caprolactone copolymer which is different from that of the sheet in the molar ratio, polyglycolic acid, polylactic acid and lactic acid/glycolic acid copolymer.

15. The method of claim the specular glossiness at 60° (GS 60°) of the artificial dura mater is 15–18% as defined by JIS Z8741.

16. A method for producing an artificial dura mater having a three layer structure comprising biodegradable and bioabsorbable synthetic polymer sheets and a reinforcement prepared from a biodegradable and bioabsorbable synthetic polymer differing from that of sheets, having a specular glossiness at 60° that is greater than 10% but not more than 20% as defined by JIS Z8741 and a haze of 80% or less as defined by JIS K7105, comprising (a) sandwiching a reinforcement between the sheets; and (b) integrally molding the sheets and the reinforcement by vacuum press.

17. A method for producing an artificial dura mater having a three layer structure comprising biodegradable and bioabsorbable synthetic polymer sheets and a reinforcement prepared from a biodegradable and bioabsorbable synthetic polymer differing from that of sheets, having a specular glossiness at 60° that is greater than 10% but not more than 20% as defined by JIS Z8741 and a total light transmittance of 30% or more as defined by JIS K7105, comprising (a) sandwiching a reinforcement between the sheets; and (b) integrally molding the sheets and the reinforcement by vacuum press.

18. A method for producing an artificial dura mater having a three layer structure comprising biodegradable and bioabsorbable synthetic polymer sheets and a reinforcement prepared from a biodegradable and bioabsorbable synthetic polymer differing from that of sheets, having a haze of 80% or less as defined by JIS K7105 and a total light transmittance of 30% or more as defined by JIS K7105, comprising a) sandwiching a reinforcement between the sheets; and (b) integrally molding the sheets and the reinforcement by vacuum press.

19. A method for producing an artificial dura mater having a three layer structure comprising biodegradable and bioabsorbable synthetic polymer sheets and a reinforcement prepared from a biodegradable and bioabsorbable synthetic polymer differing from that of sheets, having a specular glossiness at 60° that is greater than 10% but not more than 20% as defined by JIS Z8741, a haze of 80% or less as defined by JIS K7105 and a total light transmittance of 30% or more as defined by JIS K7105, comprising (a) sandwiching a reinforcement between the sheets; and (b) integrally molding the sheets and the reinforcement by vacuum press.

* * * * *